(12) United States Patent
Son

(10) Patent No.: US 9,562,890 B2
(45) Date of Patent: *Feb. 7, 2017

(54) PRE-CALIBRATED REPLACEABLE SENSOR MODULE FOR A BREATH ALCOHOL TESTING DEVICE

(71) Applicant: AK GLOBALTECH CORP., Palisades Park, NJ (US)

(72) Inventor: Matthew Hogyun Son, Palisades Park, NJ (US)

(73) Assignee: AK GLOBALTECH CORP., Palisades Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/822,748

(22) Filed: Aug. 10, 2015

(65) Prior Publication Data

US 2016/0054296 A1    Feb. 25, 2016

Related U.S. Application Data

(63) Continuation of application No. 13/559,249, filed on Jul. 26, 2012, now Pat. No. 9,103,818, which is a continuation of application No. 12/955,628, filed on Nov. 29, 2010, now Pat. No. 8,250,900, which is a continuation of application No. 11/528,979, filed on Sep. 27, 2006, now Pat. No. 7,841,224.

(60) Provisional application No. 60/776,127, filed on Feb. 22, 2006.

(51) Int. Cl.
*G01N 33/497* (2006.01)
*G01N 35/00* (2006.01)

(52) U.S. Cl.
CPC ........ *G01N 33/4972* (2013.01); *G01N 33/497* (2013.01); *G01N 2035/00326* (2013.01)

(58) Field of Classification Search
None
See application file for complete search history.

(56) References Cited

U.S. PATENT DOCUMENTS

| 5,020,628 A | 6/1991 | Bigliardi et al. |
| 5,239,492 A | 8/1993 | Hartwig et al. |

FOREIGN PATENT DOCUMENTS

| WO | 02/077636 A2 | 10/2002 |
| WO | 2005/101281 A2 | 10/2005 |

*Primary Examiner* — Robert R Raevis
(74) *Attorney, Agent, or Firm* — Im IP Law; C. Andrew Im

(57) ABSTRACT

The present invention describes a replaceable breath alcohol sensor module that can be replaced with a new pre-calibrated breath alcohol sensor module or re-calibrated. The breath alcohol sensor module requiring calibration can be removed from the body of a Breath Alcohol Testing Device (commonly called "breathalyzer" or "breathalyzer"). The breath alcohol sensor module can be separately calibrated for accurate calculation of "percent blood alcohol concentration" (% BAC) based on breath air samples and then re-installed into the breath alcohol tester or the old breath alcohol sensor module can be replaced with a new pre-calibrated breath alcohol sensor module. The present invention improves upon and/or replacing the current method of re-calibration at a breathalyzer service center.

13 Claims, 12 Drawing Sheets

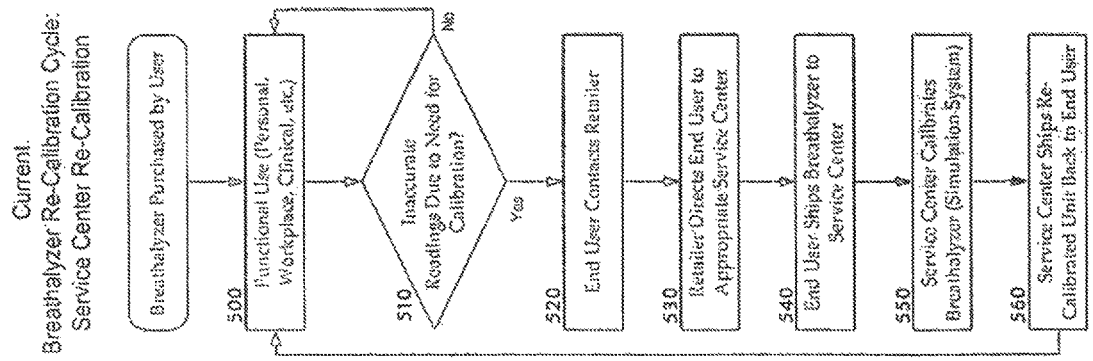
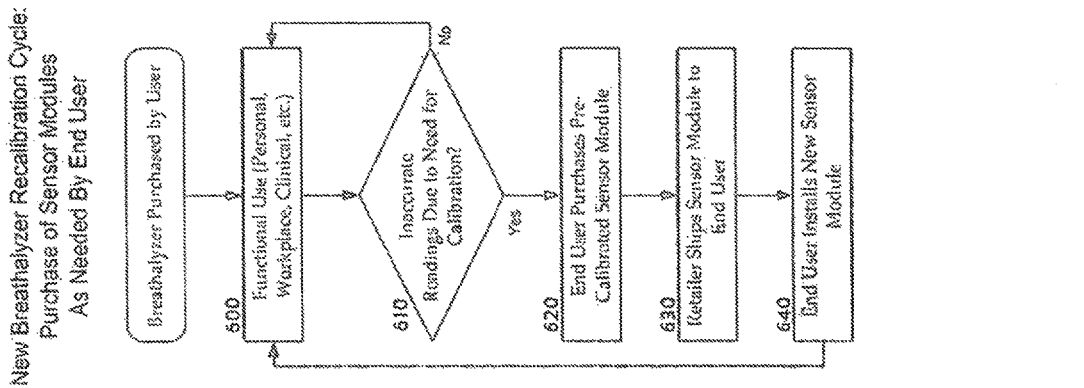
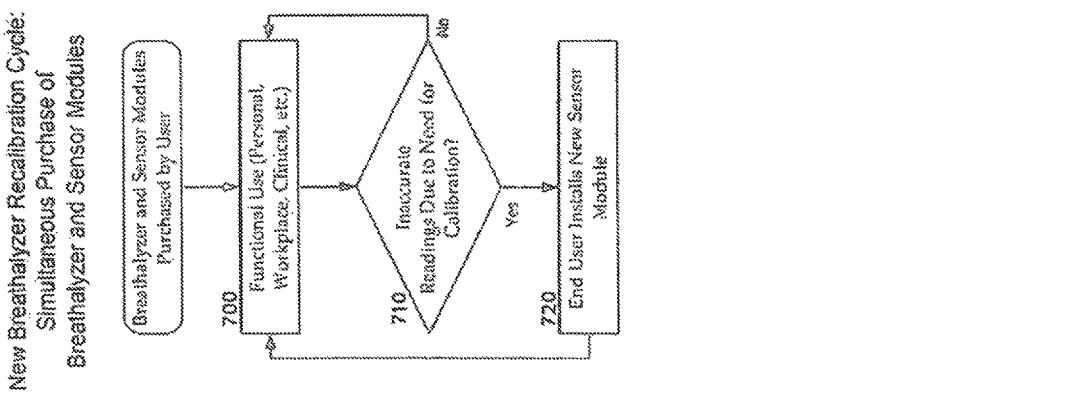

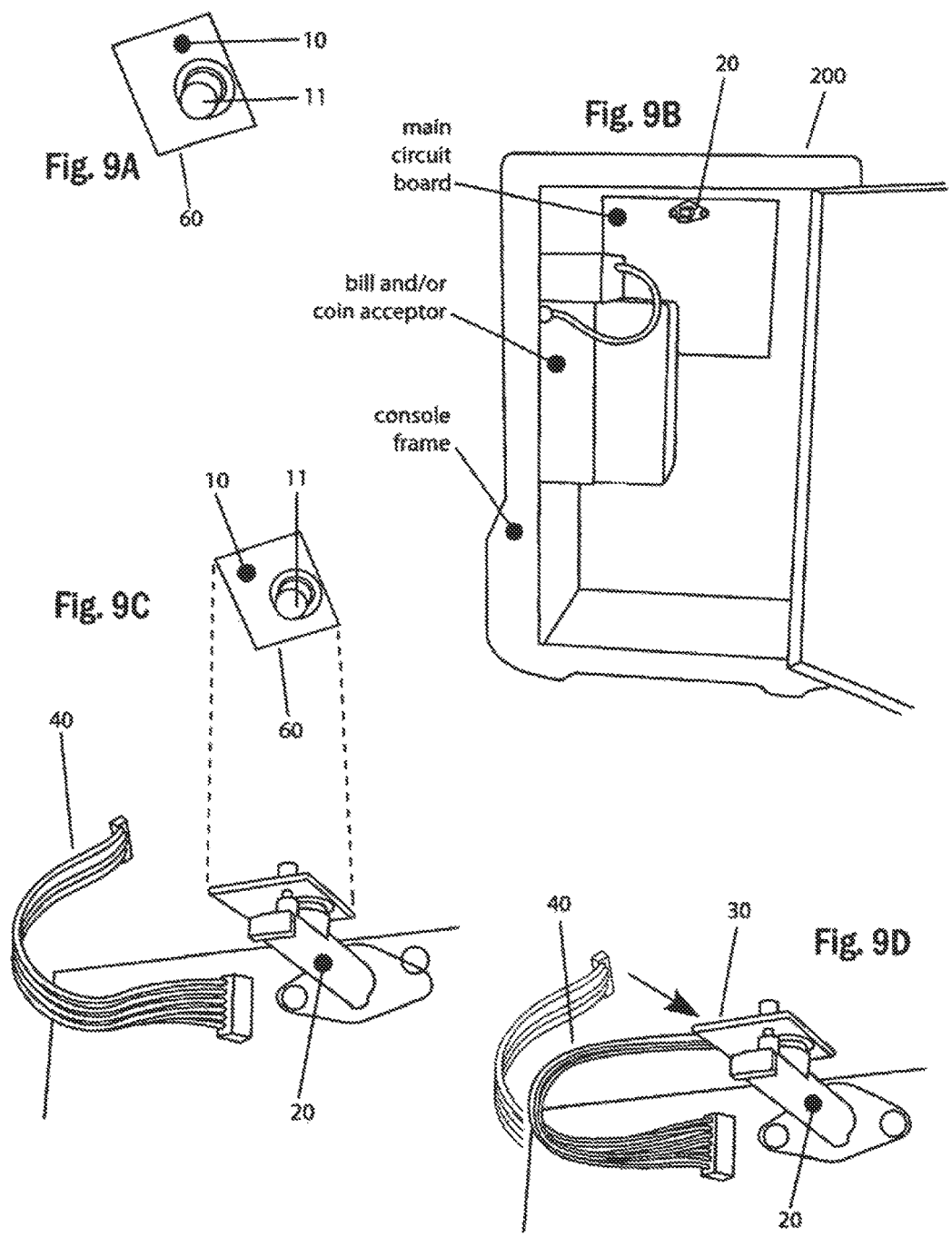

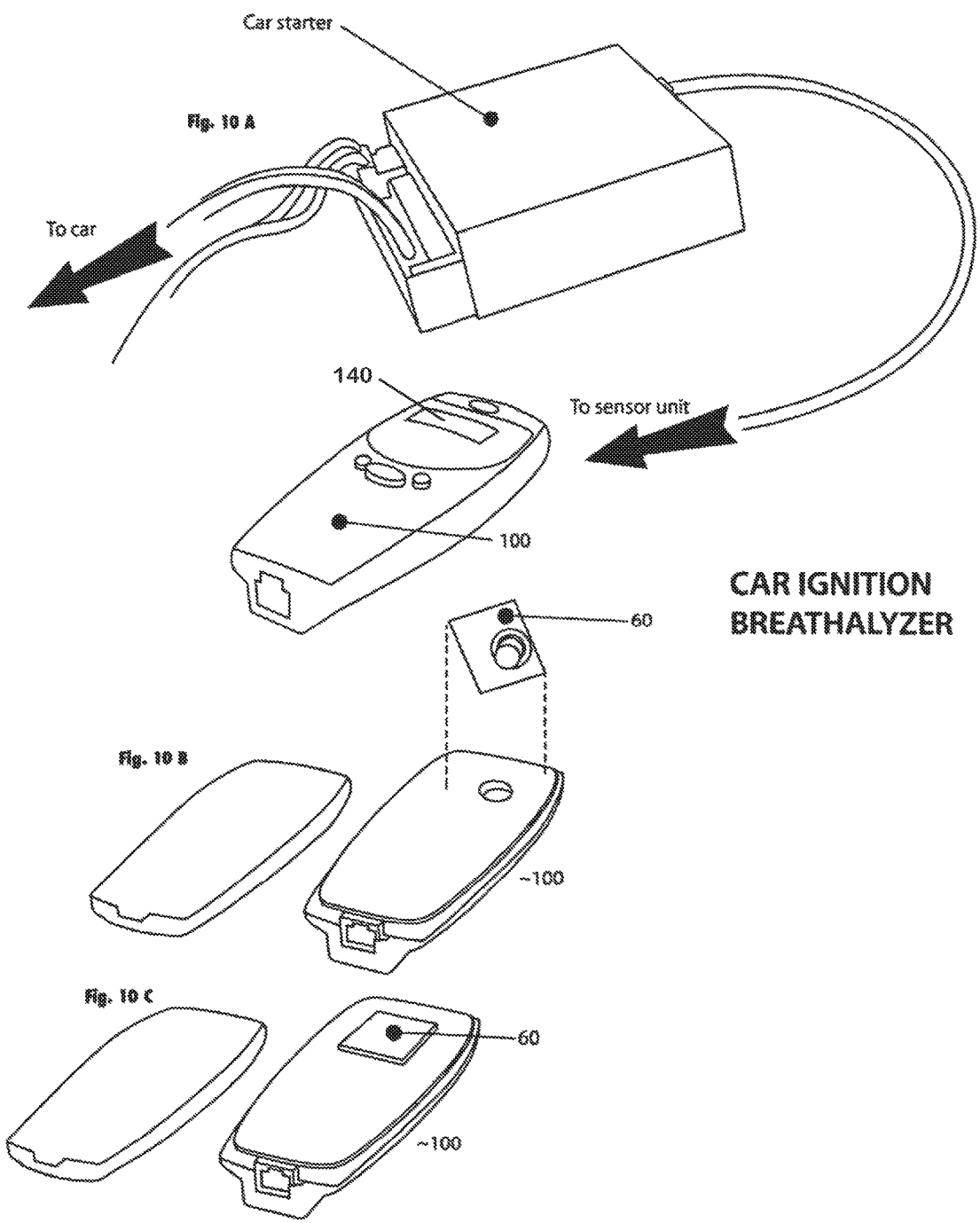

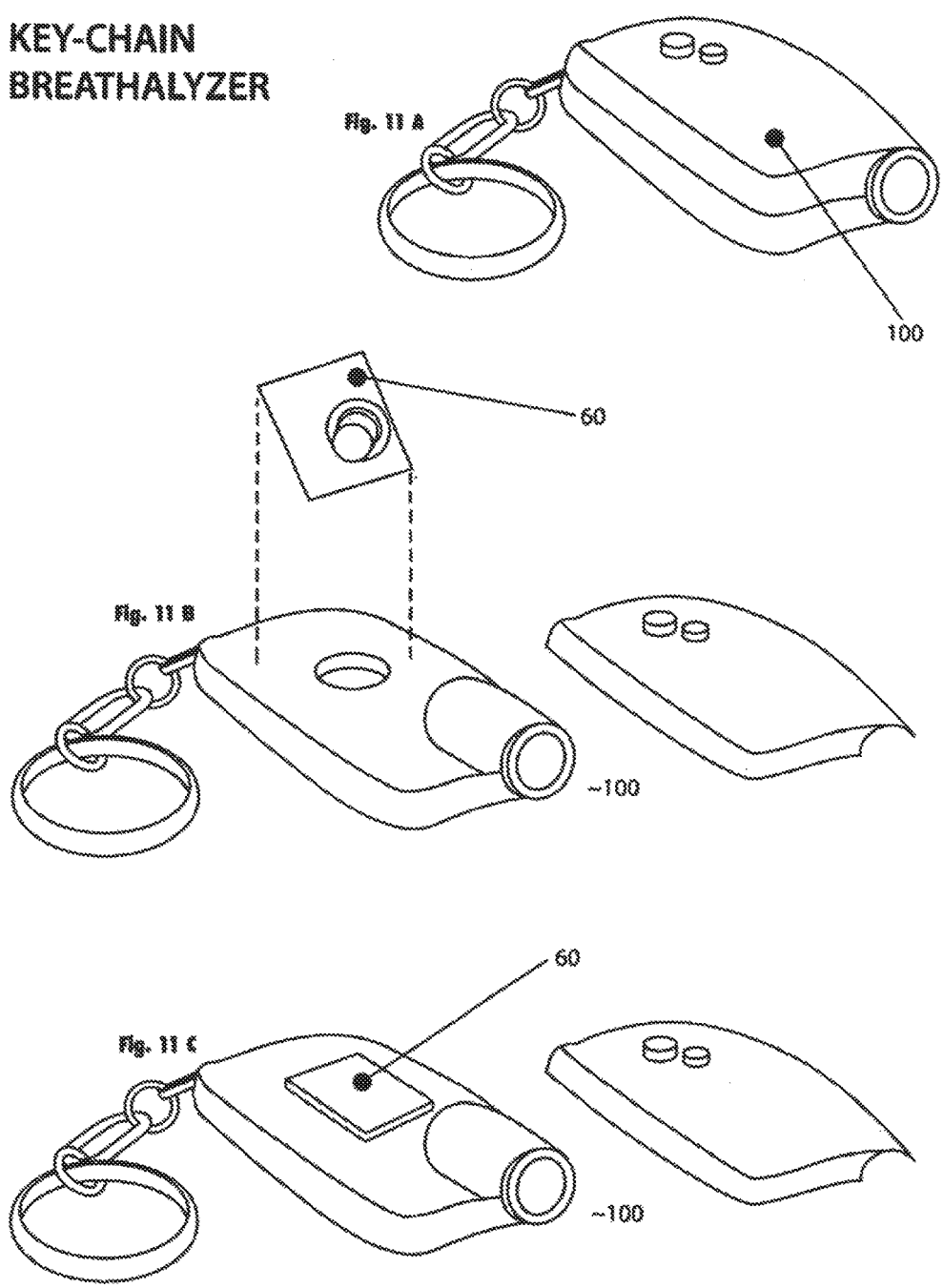

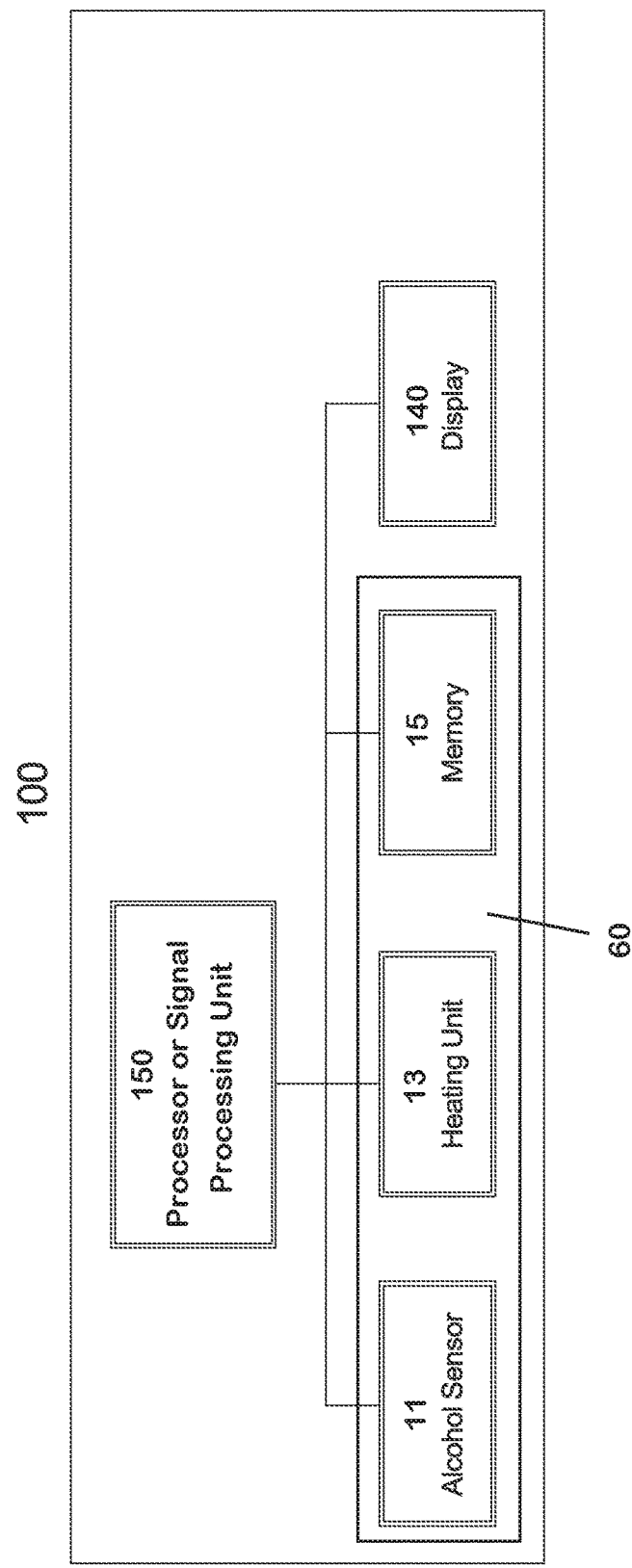

PRE-CALIBRATED REPLACEABLE SENSOR MODULE FOR A BREATH ALCOHOL TESTING DEVICE

RELATED APPLICATION

The present application is a continuation of application Ser. No. 13/559,249 filed Jul. 26, 2012, which is continuation of U.S. application Ser. No. 12/955,628 filed Nov. 29, 2010, now U.S. Pat. No. 8,250,900, which is a continuation of U.S. application Ser. No. 11/528,979 filed Sep. 27, 2006, now U.S. Pat. No. 7,841,224, which claims the benefit of U.S. Provisional Application Ser. No. 60/776,127 filed Feb. 22, 2006, each of which is incorporated herein by reference in its entirety.

FIELD OF THE INVENTION

The present invention relates to a pre-calibrated (or pre-calibrate-able), replaceable breath alcohol sensor module for use with a Breath Alcohol Testing Device. More specifically, this invention describes a breath alcohol sensor module that can be removed from the body of a breathalyzer and separately calibrated for the accurate calculation of "percent blood alcohol concentration" (% BAC) based on breath air samples, and then re-installed into the breath alcohol tester.

RELATED ART

The Breath Alcohol Testing Device is also commonly called a "breathalyser" or a "breathalyzer" (hereinafter breathalyzer), and includes both portable (PBT or Portable Breath Tester) and stationary (coin-operated or similar) units.

The availability and accessibility of the breathalyzer for both professional use (as in clinical, industrial, healthcare or workplace settings) and personal use (as in the domain of general consumers) has been expanding greatly, and with this expansion the necessity for all breathalyzers to be periodically recalibrated has created many interruptions in the market, as breathalyzers must currently be mailed or delivered to select service center locations where calibration can be done using a simulation system, making the breathalyzer unavailable to the user during this calibration period, and increasingly overwhelming the service centers as the market grows. The present invention remedies this situation by providing a method to calibrate (or re-calibrate) the breathalyzer that greatly reduces or even eliminates the time and cost involved in shipping and handling of breathalyzers and maintenance of service centers, as well as the time and utility lost by the end user.

A typical breathalyzer consists primarily of an alcohol sensor component, signal processing unit (or CPU) 150, and a display unit 140 to show results. Typically, a breath alcohol sensor is calibrated to match select calibration points using standard specifications (controlled alcohol mixtures), and the signal processing unit (or CPU) determines % BAC based on linear calculation using the calibration points. Over time (generally after several hundred tests), every breath alcohol sensor will require re-calibration as undesirable residue and foreign substances including, but not limited to, saliva, cigarette smoke residue and food particles, become trapped inside the sensor. The current system of calibration (or re-calibration) of breathalyzers by service centers takes place when a consumer or end user, with a breathalyzer in need of calibration, contacts a breathalyzer retailer (See FIG. 1). The retailer, in turn, directs the end user to ship the breathalyzer to an appropriate service center location. Upon receiving the breathalyzer, the service center uses controlled alcohol mixtures in order to re-calibrate the device according to standard specifications. When this re-calibration is complete, the breathalyzer is shipped back to the end user. This procedure for re-calibration is time-consuming and costly in terms of shipping and handling of packages, labor hours and lost utility for the end user. There are currently over 100 retailers (online and offline) and/or distributors sell breathalyzer units to consumers and end users, whereas fewer than ten (10) service center locations exist to perform traditional breathalyzer re-calibrations. Due to this discrepancy, the overall increase in sales of breathalyzer units are overwhelming the service centers with requests for re-calibration (which are both necessary and periodic for each breathalyzer), causing ever increasing delays in the processing and delivery of breathalyzers. Another issue resulting from the current system of re-calibration is that the sensor is not actually replaced, and residue buildup cannot be cleaned or removed from the sensor. This results in an increasing deterioration in overall sensor performance as residue accumulates over time, even as the sensor is re-calibrated multiple times.

In order to alleviate the time and utility lost when sending a breathalyzer for re-calibration, some end users purchase multiple breathalyzers so that at least one breathalyzer is available for use while one or more other devices are undergoing service for re-calibration. Some end users cannot afford the increase in budget in order to implement this type of stopgap measure, so compromises are made either in terms of temporary suspension of breath alcohol tests or over-taxing breathalyzer units beyond the point of necessary re-calibration (thereby allowing the breathalyzer to display increasingly inaccurate readings). In many cases, end users elect not to use breathalyzers altogether primarily due to the complications of re-calibration. Re-calibration, though an absolute necessity in the breathalyzer market, is one of the main impediments to rapid expansion of the market, especially in workplace, clinical or other professional environments where both accuracy and continuous utility are required.

Accordingly, the present invention proceeds upon the desirability of providing significant benefits for both the breathalyzer service centers and the end users by practically eliminating the loss of time and utility for end users and reducing the number of labor hours and shipping costs for service centers, all while introducing an effective solution at a cost no greater than the current service center system.

OBJECTS AND SUMMARY OF THE INVENTION

Therefore, it is an object of the present invention to provide a significantly improved replacement for the traditional method of breathalyzer re-calibration that supports market security by reducing or eliminating the time and utility lost by the end user and that also expands the market by addressing the specific needs of industrial or clinical breathalyzer applications. The present invention comprises a pre-calibrated (or pre-calibrate-able) breath alcohol sensor module, which includes both an alcohol sensor and a non-volatile memory unit to store calibration information. The pre-calibrated breath alcohol sensor module of the present invention is useable by distributors, retailers, sellers, buyers and end users to replace or eliminate traditional methods of breathalyzer re-calibration with a much more effective and efficient solution at a cost no greater and often less than any current method of re-calibration.

The breath alcohol sensor module of the present invention can be removed from the body of a breathalyzer and separately calibrated for the accurate calculation of "percent blood alcohol concentration" (% BAC) based on breath air samples, and then re-installed into the breath alcohol tester. In accordance with an exemplary embodiment of the present invention, the sensor module comprises a breath alcohol sensor as well as a non-volatile memory unit (such as EEPROM, Flash drive, NAND) to store calibration information, both of which are required to maintain an accurately calibrated state for the sensor. The present invention brings significant benefits the breathalyzer industry by giving consumers and/or other end users a better solution for re-calibrating the breathalyzer.

The present invention essentially eliminates the loss of time and utility for end users and reduces the number of labor hours and shipping costs for breathalyzer service centers. The present invention brings these significant benefits and solution to both end users and breathalyzer service centers at a cost that is no greater than the current service center system. The pre-calibrated, replaceable alcohol sensor modules of the present invention enables the end users to purchase new sensor modules when the need arises at a cost no more than (and often less than) the cost for re-calibration service (See FIG. 2). New or pre-calibrated sensor modules of the present invention ship with simple instructions for the end user to follow in order to manually replace the old sensor module requiring calibration. Because the sensor modules are pre-calibrated, shipment to the end user is immediate and without delay. The end users can purchase sensor modules simultaneously with the purchase of a breathalyzer or prior to the time that the old sensor requires re-calibration. The process of re-calibration with the sensor module of the present invention is simpler and faster than the current calibration system of utilizing a breathalyzer service center since the end user only needs to spend a few seconds swapping the old sensor module with a new sensor module in order to return the breathalyzer to its full functional use without delay (See FIG. 3).

The present invention addresses all known and future breathalyzers (or other breath alcohol testing devices) because the replaceable sensor module can be made compatible with current and future breathalyzers (or other breath alcohol testing devices). In accordance with an embodiment of the present invention, the replaceable sensor module can be applied with minimal modification to various other portable electronic devices, as long as such devices contain a display 140 capable of showing % BAC readings (e.g. digital LED display), such as portable radar detectors, portable GPS devices, mobile phones, electronic key/keychain devices, etc.

In accordance with an embodiment of the present invention, a breathalyzer user (general consumer, owner or operator of a breathalyzer compatible with the present invention) can purchase or otherwise acquire a new sensor module in order to replace the old sensor module at minimal cost and time lost for all parties involved when the breathalyzer's sensor requires re-calibration.

The traditional re-calibration system and procedure involves multiple transactions and/or communications among several entities. Typically an end user (general consumer, owner or operator of a breathalyzer) contacts the retailer from which the breathalyzer was purchased in order to report that the breathalyzer is in need of re-calibration. Currently, the large majority of all breathalyzer retailers are unable to perform re-calibration themselves, so either the retailer accepts breathalyzers requiring re-calibration from end users and ships them in bulk to a breathalyzer service center, or the retailer directs the end user to ship the breathalyzer requiring re-calibration directly to the service center. When the service center receives breathalyzers requiring re-calibration, detailed records of receipts, shipments, customer and retailer (vendor) data must be kept and maintained in order to minimize errors in processing and shipping the re-calibrated breathalyzer. Further, any problems that may arise are complicated to resolve, as these problems involve several parties that are not current with the specific situation of the end user (e.g. a single re-calibration may involve a retailer, distributor, service center and end user). With the multiple communications, transactions, record-keeping, processing and shipping that may be involved with each re-calibration, a steady increase in delays, costs and other problems can be seen in the breathalyzer market, because re-calibrations are unavoidable and periodically necessary.

The present invention eliminates many of these aforementioned problems associated with the current re-calibration system and methodology by removing entirely the need for record-keeping, processing and shipping of pre-calibrated breathalyzers beyond the common retail practice of stocking the replaceable sensor modules by the retailers and/or distributors. Delays, costs and problems associated with the current re-calibration system can be greatly reduced and even eliminated with the present invention. All breathalyzer service centers operate primarily as either breathalyzer distributors or retailers, and the service center portion of business does not generally generate significant income for these distributors or retailers, often creating a loss in profit. The present invention seeks to either greatly reduce the strain on the operation of these service centers or eliminate the need for service centers altogether. In addition, by streamlining the transactions between distributors, retailers and end users into effectively "retail only" market channels, the breathalyzer market can be made more efficient and ready for uninterrupted growth. Pre-calibrated replaceable sensor modules of the present invention will be made available to all parties involved in the breathalyzer transactions, thereby requiring only a single transaction (sale) with a single party for the end user to re-calibrate a breathalyzer, in most cases.

It is a further object of the present invention to afford simple, straightforward instructions for the handling, installation and removal of pre-calibrated replaceable breath alcohol sensor modules to the general consumer so that these operations can be performed with ease.

It is yet another object of the present invention to afford additional breath alcohol sensing functionality to a wide array of other portable electronic devices that include a method of display capable of showing % BAC readings (e.g. digital LED display). With minimal modification, the present invention can be incorporated into such portable electronic devices as portable radar detectors, portable GPS devices, mobile phones, electronic key/keychain devices, etc.

Various other objects, advantages and features of the present invention will become readily apparent from the ensuing detailed description, and the novel features will be particularly pointed out in the appended claims.

BRIEF DESCRIPTION OF FIGURES

The following detailed descriptions, given by way of example, and not intended to limit the present invention solely thereto, will be best be understood in conjunction with the accompanying figures:

FIG. 5 is a flowchart illustrating the current breathalyzer re-calibration process involving breathalyzer service centers;

FIGS. 6 and 7 are flowcharts illustrating the new breathalyzer re-calibration process in accordance with an exemplary embodiment of the present invention;

FIGS. 9A-9D are diagrams of a pre-calibrated replaceable alcohol sensor module as incorporated in a coin-operated breathalyzer in accordance with an exemplary embodiment of the claimed invention;

FIGS. 10A-10C are diagrams of a pre-calibrated replaceable alcohol sensor module as incorporated in a car ignition breathalyzer in accordance with an exemplary embodiment of the claimed invention;

FIGS. 11A-11C are diagrams of a pre-calibrated replaceable alcohol sensor module as incorporated in a key-chain breathalyzer in accordance with an exemplary embodiment of the claimed invention; and FIG. 12 is block diagram of the breathalyzer incorporating a pre-calibrated alcohol sensor module in accordance with an exemplary embodiment of the claimed invention.

DETAILED DESCRIPTION OF THE EMBODIMENTS

Figure 3:
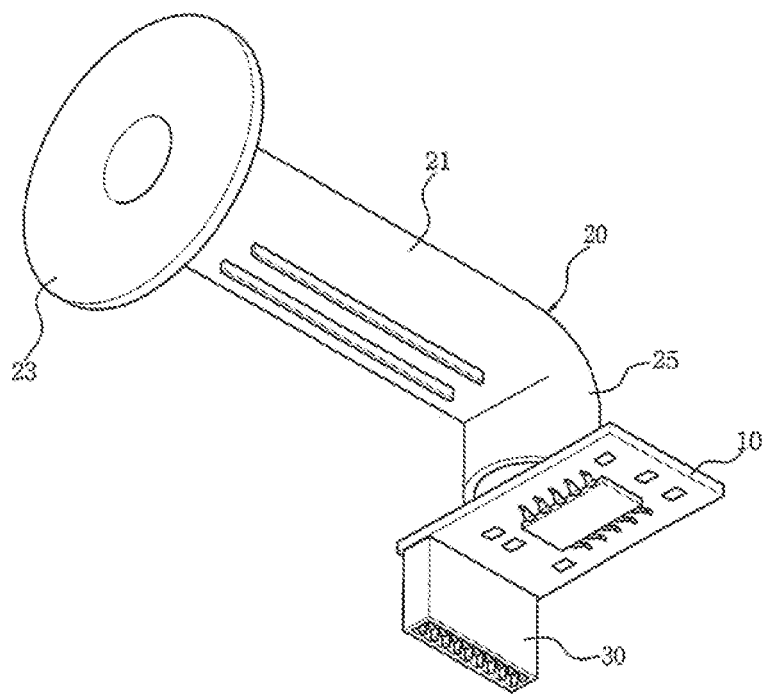
FIG. 3 is a diagram of a pre-calibrated replaceable breath alcohol sensor module attached to a breath sampling tube in accordance with an exemplary embodiment of the present invention.
Figure 4:
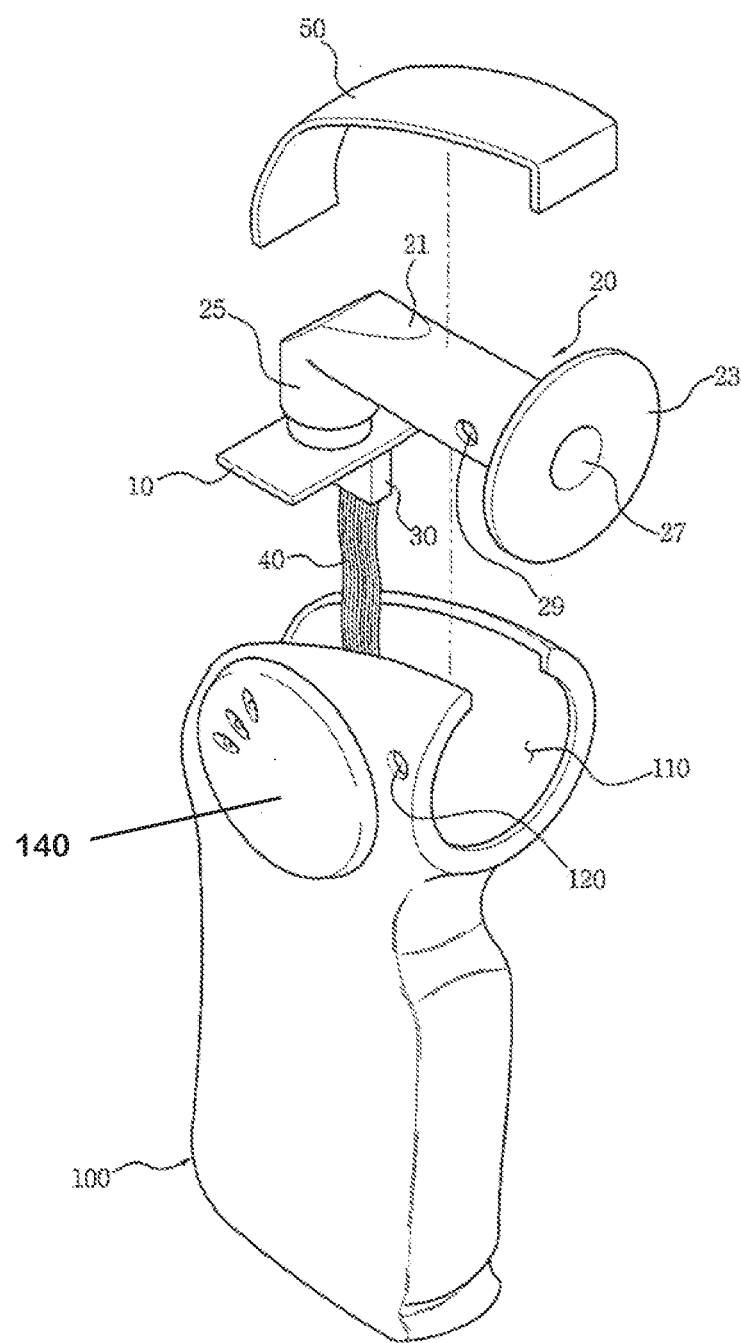
FIG. 4 is a diagram illustrating a breathalyzer unit incorporating the pre-calibrated replaceable breath alcohol sensor module of FIG. 3 in accordance with an exemplary embodiment of the present invention.
Figure 8A:
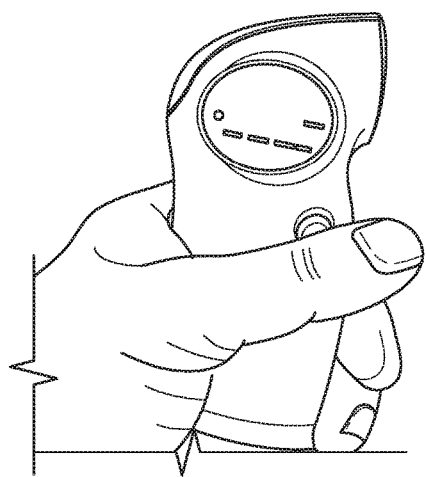
FIGS. 8A-8K depict the pre-calibrated alcohol sensor module installation process in accordance with an exemplary embodiment of the present invention.
Figure 8B:
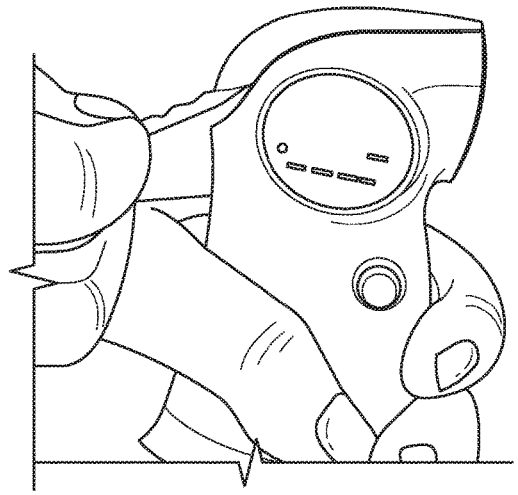
Figure 8C:
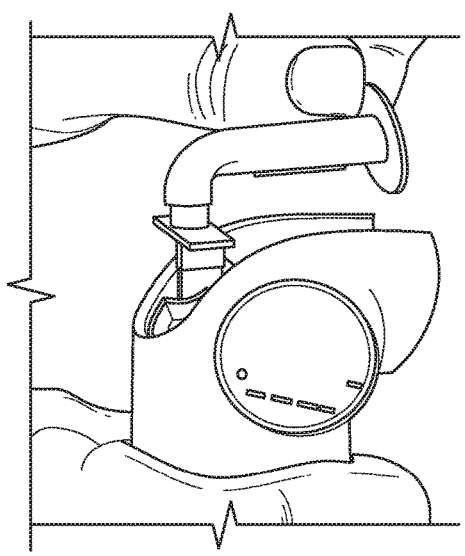
Figure 8D:
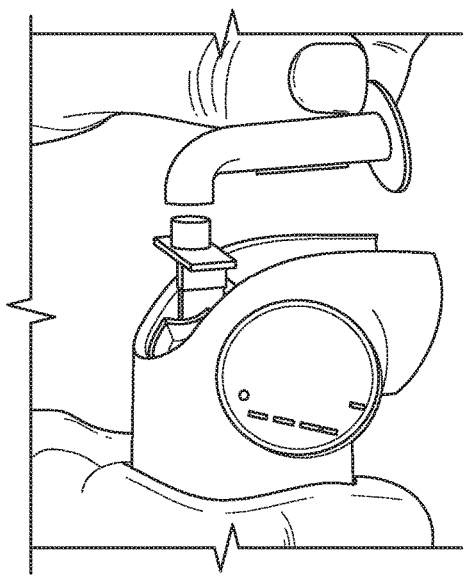
Figure 8E:
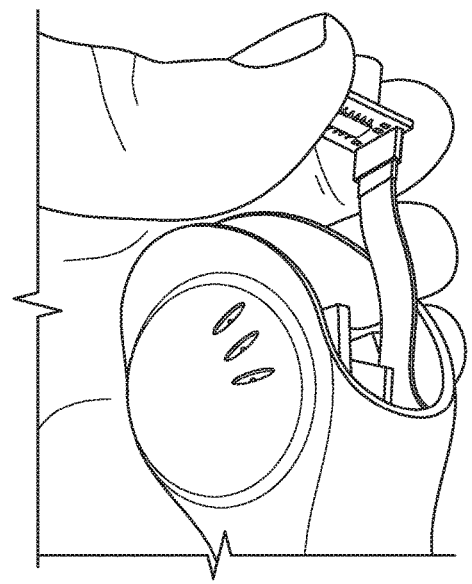
Figure 8F:
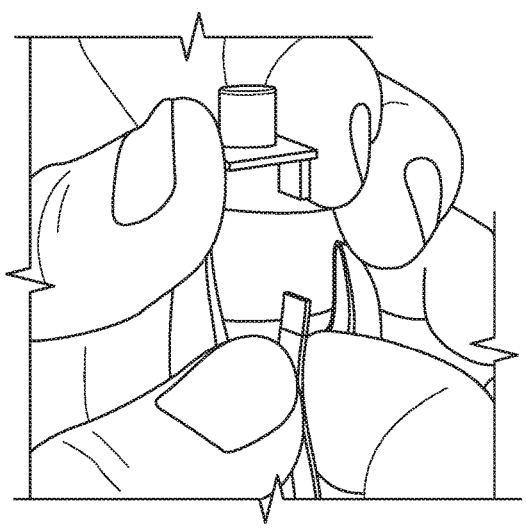
Figure 8G:
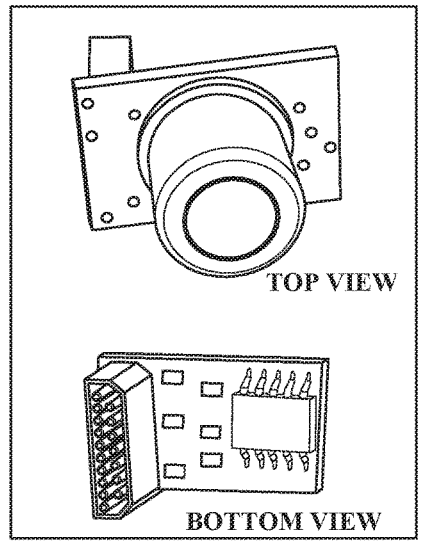
Figure 8H:
Figure 8I:
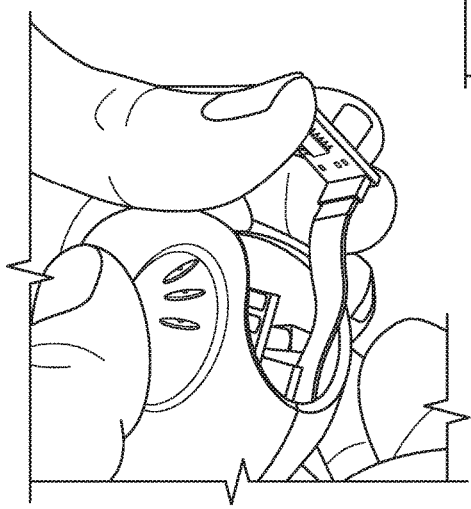
Figure 8J:
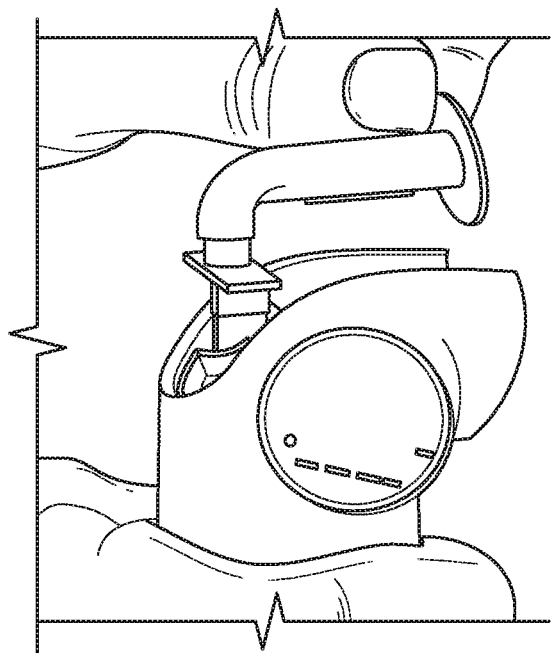
Figure 8K:
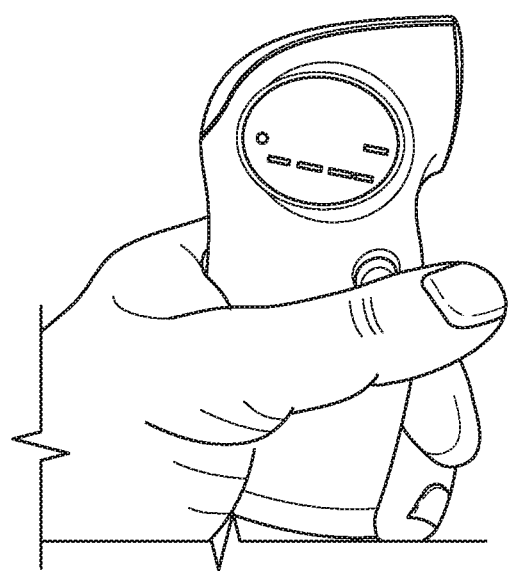

In order to eliminate the aforementioned problems with current recalibration methods, the sensor module 60 of the present invention is made compatible with a wide assortment of breathalyzers 100, as shown in FIG. 4. Breathalyzers 100 can be newly manufactured, or modified, with an easily accessible compartment 110 for both the installation and removal of the pre-calibrated breath alcohol sensor module 60 of the present invention. In accordance with an exemplary embodiment of the present invention, the accessible compartment 110 comprises a system to attach and secure the sensor module to the body of the breathalyzer 100 (e.g. attachment slots or fasteners 120), an interface 40 to electronically link the breathalyzer 100 to the adapter 30 of the sensor module 60, and a cover or faceplate 50 to enclose the sensor module 60 once it is secured within the body of the breathalyzer 100. In addition, a breath sampling tube 20 can be attached to the sensor module 60, as shown in FIG. 3, in order for the breath alcohol sensor 11 to function properly. As a matter of compatibility and convenience, the present invention describes the sensor module 60 and the breath sampling tube 20 as separate components, because of the inevitable variation in breath sampling tubes 20 across various types of breathalyzer 100. However, "pre-calibrated replaceable breath alcohol sensor module" or "sensor module" 60 may refer to the present invention with or without the attached breath sampling tube 20.

Figure 1:
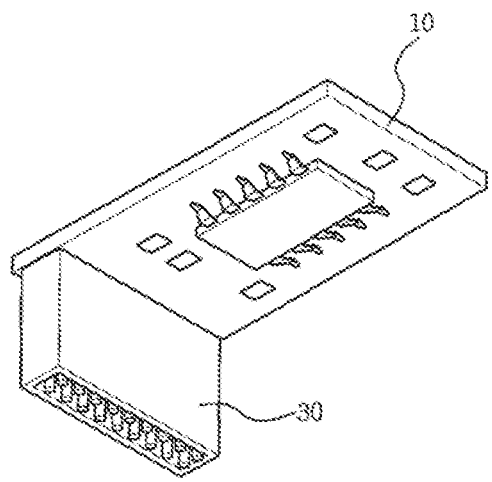
FIG. 1 is a diagram of a pre-calibrated replaceable breath alcohol sensor module in accordance with an exemplary embodiment of the present invention.
Figure 2:
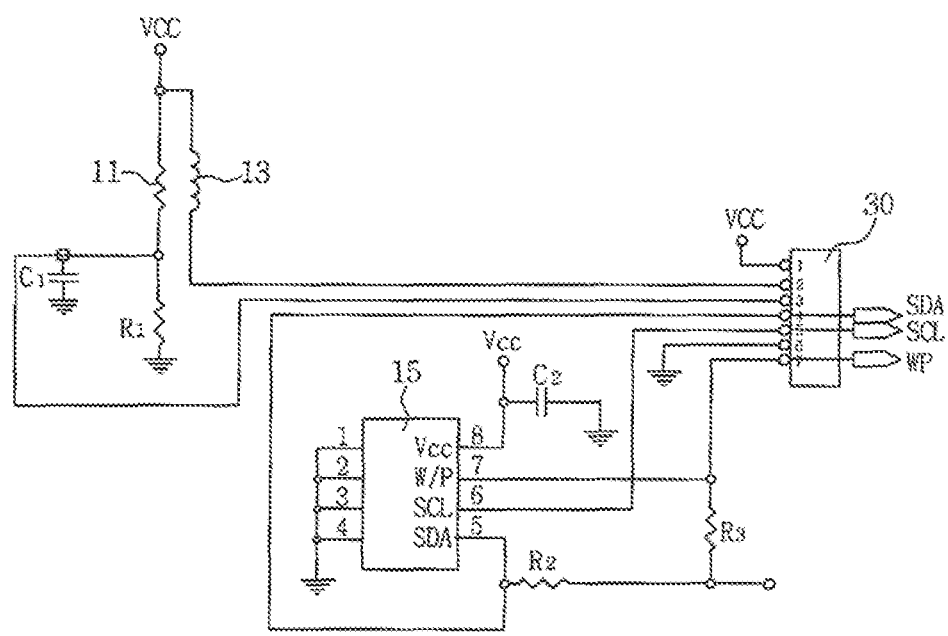
FIG. 2 is a diagram illustrating the primary circuitry of the sensor module in accordance with an exemplary embodiment of the present invention.

Turning now to FIGS. 1 and 2, there are illustrated a sensor module 60 in accordance with exemplary embodiments of the present invention. As shown in FIG. 2, the sensor module 60 comprises a printed circuit board (PCB) 10, a non-volatile memory unit 15 (located centrally on the PCB 10), an adapter 30 (located beneath the memory unit 15), a heating unit 13 and a breath alcohol sensor 11 (located opposite the memory unit and adapter in FIG. 1).

In accordance with an exemplary embodiment of the present invention, the circuitry of the sensor module 60 is operable to detect changes in conductivity according to varying levels of alcohol concentration. The heating unit 13 of the sensor module 60 is operable to warm up the breath alcohol sensor 11 to a pre-determined temperature. The non-volatile memory unit 15 stores calibration data, and the adapter 30 communicates data and readings to the breathalyzer 100.

Returning to FIG. 2, signals from the sensor module 60 to the breathalyzer's processor or signal processing unit 150 (shown in FIG. 12) through a pin 3 and the calibration data from the non-volatile memory 15 is sent through pins 4 and 5. As shown in FIG. 4, the cable 40 connects the breathalyzer 100 to the adapter 30 of the sensor module 21. In accordance with an exemplary embodiment of the present invention, the sensor module 60 (comprising the breath sampling tube 20) includes all components of a breathalyzer 100 that may suffer from residue build-up and other problems requiring re-calibration. This advantageously enables the present invention to provide a breathalyzer 100 that is as accurate as and functionally equivalent to a "new" breathalyzer 100 by simply replacing the sensor module 60 of the present invention.

The non-volatile memory 15 includes various other pins, such as pin 7 labeled as "W/P," which means "write-protect," to prevent the non-volatile memory 15 from losing the calibration data.

The primary cause for breathalyzer inaccuracy is sensor pollution, which refers to the build-up of sensor contaminants such as saliva, cigarette smoke, food particles, etc. This build-up of contaminants does not only cause sensor inaccuracy, but also reduces the overall lifetime of the sensor 11, because the residue cannot simply be removed. This means that even if the sensor is re-calibrated or adjusted, it can never be as efficient or accurate as a new sensor 11. The buildup of contaminants within the breath sampling tube 20 can also affect functionality and accuracy of the breath alcohol sensor 11, but to a lesser extent than sensor pollution.

In accordance with an exemplary embodiment of the present invention, the sensor module 70 comprises a breath sampling tube 20 attached therein, as shown in FIG. 3. This "complete" module 70 replaces any and all components of a breathalyzer 100 that is subject to contaminant build-up. The breath sampling tube 20 is attached directly above the breath alcohol sensor 11, so that the sensor can process alcohol readings from a breath sample.

As can be seen in FIG. 3, the breath sampling tube 20 consists of a long cylindrical tube 21 for the blown air to travel through, a mouthpiece slot 27, and a bent or curved section 25 to direct air toward the breath alcohol sensor 11.

In accordance with an exemplary embodiment of the present invention, FIG. 4 shows how the pre-calibrated replaceable breath alcohol sensor module 70 (with the attached breath sampling tube 20) is installed into a compatible breathalyzer 100. For example, the breath sampling tube 20 comprises an attachment slot 29 and the breathalyzer 100 comprises an attachment slot 120 to secure the sensor module 70 in the accessible compartment 110 of the breathalyzer 100. A cable 40 electronically links the sensor module 70 with the breathalyzer's signal processing unit 150 (shown in FIG. 12). The attachment slots 29, 120 can be secured using screws, pins or other known fastening means. The breathalyzer 100 also comprises a cover 50 for enclosing the sensor module 70 after installation to maintain a consistent exterior appearance of the breathalyzer 100.

FIG. 5 is a flowchart describing the current state of the breathalyzer re-calibration procedure. Typically, the user purchases the breathalyzer 100 for work (e.g., a police officer can use it for sobriety testing), clinical studies, personal use, etc. After many repeated uses in step 500, the breathalyzer 100 generally requires re-calibration due to residue build-up and/or other problems discussed herein. In step 510, an inquiry is made to determine if the breathalyzer 100 is requires re-calibration. If the inquiry in step 510 is answered in the negative, the breathalyzer 100 can be used to calculate or measure % BAC in step 500.

However, if the inquiry in step 510 is answered in the affirmative, the user contacts the retailer in step 520 and the retailer directs the user to an appropriate service center in step 530. The user ships the breathalyzer 100 to the service center in step 540.

Upon receipt of the breathalyzer 100, the service center calibrates the breathalyzer, e.g., using the simulation system, in step 550, and ships the re-calibrated breathalyzer back to the user in step 560, thereby enabling the user to return to step 500 and use the breathalyzer 100 to calculate or measure % BAC.

FIG. 6 is a flowchart describing the breathalyzer re-calibration procedure in accordance with an exemplary embodiment of the present invention wherein the user purchases the new pre-calibrated sensor module 60 or 70 only if it is needed. After many repeated uses of the breathalyzer 100 to calculate or measure % BAC in step 600, the breathalyzer 100 generally requires re-calibration due to residue build-up and/or other problems discussed herein. Typically, the breathalyzer 100 requires re-calibration after being used for 200-300 times (varying depend on the factors noted herein). Alternatively, the breath alcohol sensor module 60, 70 or the signal processing unit 150 of the breathalyzer 100 can perform tests periodically or upon request by the operator (i.e., pressing a button on the housing of the breathalyzer 100) to determine if the breath alcohol sensor 11 requires re-calibration. In step 610, an inquiry is made to determine if the breathalyzer 100 requires re-calibration. If the inquiry in step 610 is answered in the negative, the breathalyzer 100 can be used to calculate or measure % BAC in step 600.

However, if the inquiry in step 610 is answered in the affirmative, the user purchases pre-calibrated sensor module 60 or 70 of the present invention in step 620. Alternatively, the user can purchase the pre-calibrated sensor module 60 or 70 over the phone or internet in step 620 and the retailer ships a new pre-calibrated sensor module 60 or 70 to the user in step 630. The user installs the new pre-calibrated sensor module 60 or 70 in the breathalyzer 100 in step 640, thereby enabling the user to return to step 600 and use the breathalyzer 100 to calculate or measure % BAC.

FIG. 7 is a flowchart describing the breathalyzer re-calibration procedure in accordance with an exemplary embodiment of the present invention wherein the user purchases the breathalyzer 100 and additional new pre-calibrated sensor module(s) 60 or 70. After many repeated use of the breathalyzer 100 to calculate or measure % BAC in step 700, the breathalyzer 100 generally requires re-calibration due to residue build-up and/or other problems discussed herein. In step 710, an inquiry is made to determine if the breathalyzer 100 requires re-calibration. If the inquiry in step 710 is answered in the negative, the breathalyzer 100 can be used to calculate or measure % BAC in step 700.

However, if the inquiry in step 710 is answered in the affirmative, the user installs the new pre-calibrated sensor module 60 or 70 in the breathalyzer 100 in step 720, thereby enabling the user to return to step 700 and use the breathalyzer 100 to calculate or measure % BAC.

In accordance with an exemplary embodiment of the present invention, FIGS. 8A-K depict how a user can install a pre-calibrated alcohol sensor module 60 of the present invention. The user prepares to install a pre-calibrated alcohol sensor module 60 in a breathalyzer 100 in FIG. 8A. The user can use a flat, sharp tool to carefully open the top cover 50 of the breathalyzer 100 in FIG. 8B, and lifts the breath sampling tube 20 to access the alcohol sensor module 60 in FIG. 8C. Next, the user removes the breath sampling tube 20 which should remove easily in FIG. 8D, and then carefully raises the alcohol sensor module 60 from the body of the breathalyzer 100, taking care not to detach the cable 40 from the body of the breathalyzer 100 in FIG. 8E. The cable 40 is removed from the adapter or slot 30 underneath the alcohol sensor module 60 in FIG. 8F and a new pre-calibrated alcohol sensor module 60 is prepared for insertion in FIG. 8G. The cable 40 is inserted into the new alcohol sensor module 60 in FIG. 8H and the alcohol sensor module 60 is placed in its original position in FIG. 8I. The breath sampling tube 20 is then reattached directly on to the alcohol sensor module 60 in FIG. 8J and the cover 50 is reattached onto the top of the body of the breathalyzer 100 in FIG. 8K.

The present invention, having been described, will make apparent to those skilled in the art that the same may be varied in many ways without departing from the spirit and scope of the invention. Any and all such modifications are intended to be included within the scope of the following claims. For example, FIG. 4 shows distinct and defined locations for components such as attachment slots 29, 120 and cover 50, but as breathalyzers 100 are manufactured in many different styles and shapes, only one example of how the pre-calibrated sensor module 60 or 70 of the present invention is installed in a particular breathalyzer (or the fitment of the pre-calibrated sensor module 60 or 70 to a particular breathalyzer) is shown for simplicity. It is appreciated that the present invention is not limited to the breathalyzer 100 example given in FIG. 4, either in terms of fitment, attachment methods or specific installation/removal procedures. Other types of breathalyzers include, for example, portable breathalyzers, coin-operated commercial units (FIGS. 9A-9D), key-chain breathalyzers (FIGS. 11A-11C) and car ignition breathalyzers (FIGS. 10A-10C). The replaceable breath alcohol sensor module 60, 70 of the present invention is intended for use in all such varieties of breathalyzers.

What is claimed:

1. A pre-calibrated replaceable alcohol sensor module, comprising:
   a printed circuit board (PCB);
   an alcohol sensor configured to receive a breath air sample and to measure blood alcohol concentration (BAC) based on analysis of the breath air sample; and
   a circuitry mounted on the PCB and configured to transmit measured BAC from the alcohol sensor to a signal processing unit of a breathalyzer and configured to transmit pre-calibrated data of the alcohol sensor from a non-volatile memory to the signal processing unit of the breathalyzer to provide measurement of the breath air sample; and wherein the pre-calibrated replaceable alcohol sensor module is installable in the breathalyzer to replace an existing pre-calibrated replaceable alcohol sensor module in the breathalyzer after being used for a predetermined number of times.

2. The replaceable alcohol sensor module of claim 1, wherein the pre-calibrated replaceable alcohol sensor module removably connects to the breathalyzer.

3. The replaceable alcohol sensor module of claim 2, further comprising an adapter for removably connecting the pre-calibrated replaceable alcohol sensor module to the breathalyzer.

4. The replaceable alcohol sensor module of claim 1, wherein the breathalyzer is one of the following: a portable breathalyzer, a coin-operated breathalyzer, a key-chain breathalyzer or a car ignition breathalyzer.

5. The replaceable alcohol sensor module of claim 1, wherein the breathalyzer comprises a compartment to house the pre-calibrated replaceable alcohol sensor module and a cover to enclose the pre-calibrated replaceable alcohol sensor module within the breathalyzer.

6. The replaceable alcohol sensor module of claim 1, further comprising a heating unit to warm up the alcohol sensor to a predetermined temperature.

7. The replaceable alcohol sensor module of claim 1, wherein the alcohol sensor is operable to detect changes in conductivity according to varying levels of alcohol concentration in the breath air sample.

8. A breathalyzer, comprising:
a signal processing unit;
a pre-calibrated replaceable alcohol sensor module comprising:
  a printed circuit board (PCB);
  an alcohol sensor configured to receive a breath air sample and to measure blood alcohol concentration (BAC) based on analysis of the breath air sample; and
  a circuitry mounted on the PCB and configured to transmit measured BAC from the alcohol sensor to the signal processing unit of the breathalyzer and configured to transmit pre-calibrated data of the alcohol sensor from a non-volatile memory to the signal processing unit of the breathalyzer to provide measurement of the breath air sample;
an interface to connect the pre-calibrated replaceable alcohol sensor module to the signal processing unit;
a display to display the measurement of the breath air sample from the signal processing unit of the breathalyzer to a user; and
wherein the pre-calibrated replaceable alcohol sensor module is replaceable with another pre-calibrated replaceable alcohol sensor module after being used for a predetermined number of times.

9. The breathalyzer of claim 8, wherein the breathalyzer is one of the following: a portable breathalyzer, a coin-operated breathalyzer, a key-chain breathalyzer or a car ignition breathalyzer.

10. The breathalyzer of claim 8, wherein the pre-calibrated replaceable alcohol sensor module comprises a heating unit to warm up the alcohol sensor to a predetermined temperature.

11. The breathalyzer of claim 8, wherein the breath alcohol sensor of the pre-calibrated replaceable alcohol sensor module is operable to detect changes in conductivity according to varying levels of alcohol concentration in the breath air sample.

12. A method of maintaining a breathalyzer having a pre-calibrated replaceable alcohol sensor module in a calibrated state, comprising the steps of:
determining if the pre-calibrated replaceable alcohol sensor module requires calibration, the pre-calibrated replaceable alcohol sensor module comprising:
  a printed circuit board (PCB);
  an alcohol sensor configured to receive a breath air sample and to measure blood alcohol concentration (BAC) based on analysis of the breath air sample; and
  a circuitry mounted on the PCB and operable to transmit measured BAC from the alcohol sensor to a signal processing unit of the breathalyzer and operable to transmit pre-calibrated data of the alcohol sensor from a non-volatile memory to the signal processing unit of the breathalyzer to provide measurement of the breath air sample; and
replacing the pre-calibrated replaceable alcohol sensor module with another pre-calibrated replaceable breath alcohol sensor module after being used for a predetermined number of times.

13. The method of claim 12, wherein the step of replacing comprises the steps of:
disconnecting the pre-calibrated replaceable alcohol sensor module from the breathalyzer; and
connecting said other pre-calibrated replaceable alcohol sensor module to the breathalyzer.

* * * * *